United States Patent [19]

Madsen

[11] Patent Number: 4,553,838
[45] Date of Patent: Nov. 19, 1985

[54] OPTICAL INSPECTION SYSTEM

[75] Inventor: Kay Madsen, Saratoga, Calif.

[73] Assignee: Eaton Corporation, Cleveland, Ohio

[21] Appl. No.: 368,547

[22] Filed: Apr. 15, 1982

[51] Int. Cl.$^4$ ............... G01N 21/88; G01N 21/90
[52] U.S. Cl. ................................. 356/237; 356/240; 250/563
[58] Field of Search ............... 250/223 B, 563, 577, 250/214 AL, 214 B; 356/237, 239, 240; 358/106; 324/103 P, 99 D; 340/753, 760, 762

[56] References Cited

U.S. PATENT DOCUMENTS

| | | | |
|---|---|---|---|
| 3,749,923 | 7/1973 | Husome | 250/223 B |
| 3,805,036 | 4/1974 | Michaud et al. | 324/103 P X |
| 3,818,495 | 6/1974 | Sagara et al. | 356/227 |
| 3,919,531 | 11/1975 | Bobel, II et al. | 250/563 |
| 3,920,970 | 11/1975 | Slaker | 356/237 |
| 3,934,136 | 1/1976 | Schoon | 250/563 |
| 4,079,416 | 3/1978 | Faani et al. | 358/106 |
| 4,251,769 | 2/1981 | Ewert et al. | 324/103 P X |
| 4,348,666 | 9/1982 | Ogita | 340/753 |
| 4,428,672 | 1/1984 | Allard et al. | 356/237 |

Primary Examiner—Vincent P. McGraw
Assistant Examiner—S. A. Turner
Attorney, Agent, or Firm—C. H. Grace; M. L. Union

[57] ABSTRACT

An optical inspection system (10) for deriving information from an item (12) to be inspected includes a light source (14), an optical reader (16) responsive to the light reflected from the inspected item for deriving an analog signal (83) indicative of information sensed on the inspected item, a threshold circuit (24) for setting a dynamic threshold used to convert the analog signal into a binary signal (144) indicative of the information sensed on the inspected item. The threshold circuit includes a high peak detector (100) and a low peak detector (102) responsive, respectively, to the highest peak and to the lowest peak in said analog signal for generating a high and low signal, respectively, indicative thereof. A threshold setting circuit (132) is responsive to the high signal and the low signal to set a threshold therebetween. A comparator (22) compares the analog signal with the set threshold and converts the analog signal to a binary signal indicative of the information sensed on the inspected item. An indicator (26) is provided which is responsive to the high and low signals for generating a dynamic visual indication of the difference or contrast between the high and low signals and a visual indication of the light level.

24 Claims, 4 Drawing Figures

OPTICAL INSPECTION SYSTEM

BACKGROUND OF THE INVENTION

1. Field of the Invention

The present invention relates to an optical inspection system and more particularly to an optical inspection system having a threshold circuit responsive to the highest and lowest peak in an analog signal representative of information derived from an inspected item. The threshold circuit includes threshold setting means for setting a threshold in response to the highest and lowest peaks sensed. A comparator means compares the analog signal with the set threshold and converts the analog signal to a binary signal. An indicator means is provided responsive to the highest and lowest peaks in the analog signal for generating a visual indication of the difference between the highest and lowest peaks.

2. Background of the Invention

There are many known optical inspection systems in the prior art. Generally, the known systems are quite complex and process large amounts of data which reduces the speed of the system and increases the cost. The present invention overcomes some of the disadvantages associated with the prior art systems by sensing less information but insuring that the sensed information is significant. Because less information is sensed, less data processing is required and a faster, less expensive system is provided.

Additionally, prior art systems have had problems compensating for the contrast on an item to be inspected. The ambient light reflecting off an object to be inspected can vary rapidly and cause false readings in the system. The present invention overcomes this disadvantage by the utilization of a threshold circuit which automatically compensates for changes in the ambient light and by providing the user of the system with an instantaneous visual indication of the contrast present on an item to be inspected.

SUMMARY OF THE INVENTION

The present invention relates to a new and improved optical inspection system for deriving information from an item to be inspected which includes a radiation source, a reader responsive to the radiation reflected from the item to be inspected and for establishing an analog signal indicative of the information sensed on the item to be inspected and a threshold circuit for setting a dynamic threshold used to convert the analog signal into a binary signal. The threshold circuit is responsive to the highest and lowest peaks in the analog signal indicative of derived information from the inspected item and includes threshold setting means responsive to the highest and lowest peaks for setting a threshold therebetween. A comparator is provided for comparing the analog signal with the set threshold and for converting the analog signal to a binary signal. Additionally, an indicator means is provided which is responsive to the highest and lowest peaks for generating an instantaneous visual indication of the difference between the highest and the lowest peaks.

A further provision of the present invention is to provide a new and improved optical inspection system for sequentially inspecting a plurality of like items including a source of illumination and an optical reader responsive to the light reflected from the item to be inspected for establishing an analog signal having a plurality of serial bits indicative of the information sensed on the inspected item. The optical reader includes a plurality of sensor elements arranged in an array and which are sequentially polled each time an item is to be inspected to establish the analog signal wherein each serial bit of analog information for each inspected item is indicative of the information sensed on the inspected item by one of the sensor elements. The threshold circuit is provided for setting a dynamic threshold which is used to convert the analog signal to a binary signal having a plurality of serial bits indicative of the information sensed on the inspected item by each of the sensor elements. The threshold circuit includes high and low peak detectors responsive to the highest peak and lowest peaks from the plurality of sensor elements in the analog signal and threshold setting means responsive to the highest and the lowest peaks for setting a threshold between the highest and lowest peaks. A comparator compares the analog signal from each of the plurality of sensor elements with the set threshold and converts the analog signal to a binary signal. Indicator means is provided responsive to the highest and lowest peaks for generating an indication of a difference therebetween.

Still another provision of the present invention is to provide a new and improved label inspection system for sequentially inspecting a plurality of items having labels therein including a light source for illuminating the items to be inspected, in optical reader for establishing an analog signal having a plurality of serial bits indicative of the information sensed on the inspected items. The optical reader includes a plurality of sensor elements which are sequentially polled each time an item is to be inspected to establish the analog signal which has a plurality of serial analog bits wherein each bit is indicative of the information sensed by one of the polled sensor elements. A threshold circuit is provided for setting a dynamic threshold which is used to convert the analog signal into a binary signal having a plurality of serial bits wherein each bit is indicative of the information sensed by one of the polled sensor elements. The threshold circuit includes a high peak detector and a low peak detector responsive, respectively, to the highest and lowest peaks in the analog signal and threshold setting means responsive to the highest and lowest peaks for setting a threshold therebetween. A comparator means compares the analog signal with the set threshold and converts the analog signal to a binary signal indicative of the information sensed on the inspected item. An indicator is provided responsive to the highest peak and the lowest peak for generating a visual indication of the contrast or difference between the highest and lowest peaks.

DESCRIPTION OF THE PREFERRED EMBODIMENT

Figure 1:
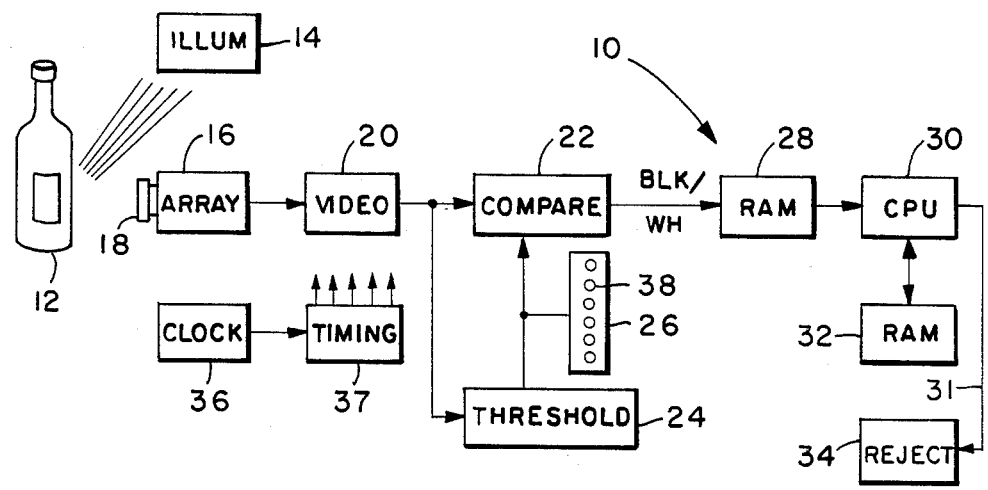
FIG. 1 is a block diagram illustrating the optical inspection system of the present invention.

Referring to the figures and, more particularly, to FIG. 1, an optical inspection system 10 is schematically illustrated. The optical inspection system 10 is operable to sense information from an object 12 to be inspected and compare the sensed information with a reference set of information to determine whether the sensed information corresponds to the reference information and to what extent the reference information does not correspond to the actual sensed information. The object to be inspected, 12, is illuminated by a suitable light source 14 and light reflected from the object 12 is sensed by a diode matrix array 16 which preferably may be a 12×38 diode matrix array such as manufactured by Reticon. A lens 18 may be provided on the array 16 for adjusting the focus and f-stop. While only one item 12 is illustrated as being inspected in FIG. 1, it should be appreciated that a plurality of items 12 can be sequentially passed by the array 16 and inspected by the present system 10.

The diode matrix array 16 includes a plurality of diodes which are sequentially polled each time an item 12 is to be examined. A complete scan through all diodes in the array constitutes a frame. The sequential scanning of the diodes in the array 16 establishes a serial analog signal indicative of the information sensed by each diode in the array for each inspected item 12. Each item 12 sensed by the array 16 establishes an analog signal having a plurality of serial analog bits of information wherein each bit corresponds to the information sensed by one of the diodes of the array 16. The output of the array 16 is directed to a video circuit 20 which processes the serial analog signal in a manner more fully defined hereinbelow, and directs it to the input of a compare circuit 22 and a threshold circuit 24.

The threshold circuit 24 is operable to sense the highest peak and the lowest peak in each serial analog signal and set a threshold between the highest peak and the lowest peak. The set threshold established by the threshold circuit 24 is directed to an input of the compare circuit 22 along with the analog signal from the output of the video circuit 20. The compare circuit then converts each serial bit of the analog signal from the video circuit 20 into a binary bit. The binary output of the comparator circuit 22 is a serial binary signal wherein each bit has a high condition when the corresponding analog bit from the video circuit 20 is greater than the set threshold and a low condition when the corresponding analog bit is less than the set threshold.

The binary output of the comparator circuit 22 is directed to a RAM 28 which directs the signal to a central processing unit 30. A RAM 32 or EE PROM such as manufactured by Intel includes reference information stored therein which is indicative of the information sensed when the object 12 corresponds to a perfect reference object. The central processing unit 30 compares the information in the RAM or EE PROM 32 with the information in the RAM 28 to make a determination of whether the inspected item 12 is a good item which corresponds to the reference stored in RAM 32 or is a bad item when there is a predetermined amount of variance between the object 12 and the reference pattern stored in the reference RAM 32. If the object 12 sensed is unacceptable, a reject mechanism 34 will be energized to reject the object 12. The central processing unit 30 will make a decision based on the variance between the reference and sensed item to determine if the item inspected is a good item or a bad item. A threshold will be programmed in the central processing unit 30 to set the allowed predetermined variance between the reference and the sensed item. If the allowed predetermined variance is exceeded, the item 12 will be rejected and if the allowed predetermined variance is not exceeded, the item will be accepted. The threshold variance can be changed in a well known manner by the operator of the system 10.

An indicator means 26 is connected to the output of the threshold circuit 24 and provides a visual indication of the difference between the highest and lowest peaks in each analog signal. The indicator means 26 includes a plurality of light emitting diodes 38 which are turned on to provide the user of the system with an indication of the contrast and light level on the object 12, as will be more fully described hereinbelow.

A clock 36 and timing circuit 37 are also provided for clocking the various signals through the components of the system and for maintaining synchronization between the various circuits as is well known in the art.

Figure 2:
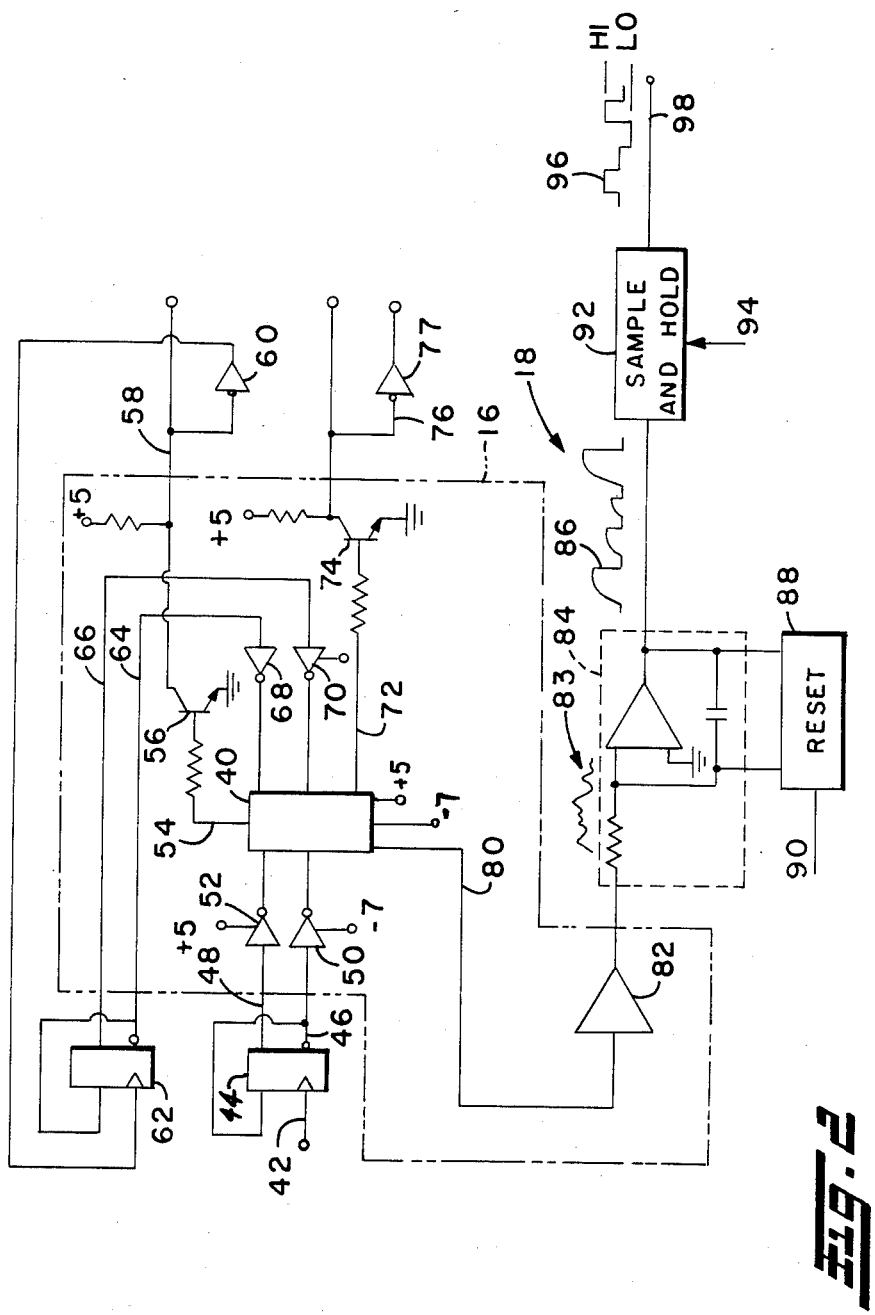
FIG. 2 is a detailed schematic drawing of the array and video circuits disclosed in FIG. 1.

Referring more particularly to FIG. 2, the array circuit 16 includes a 12×38 pixel array 40. The array 40 includes a plurality of light emitting diodes, not illustrated, which are arranged in a 12×38 array. Each of the diodes is operable to sense reflected light from the object 12 to gather information about the object 12. The array 40 can be purchased from various vendors such as Reticon and operates in a well-known manner.

A periodic clock input is provided on line 42 to a flip-flop 44 having a pair of outputs 46, 48 which are connected to digital inverters 50 and 52, respectively, to inputs of the array 40. The flip flop 44 provides two clock pulses to the array 40, one via each of the digital inverters 50, 52, every time a clock pulse is applied to line 42. The particular Reticon array utilized in the present invention requires a clock and a $\overline{\text{clock}}$ input for sequencing the array 40. It should be appreciated that other arrays could be utilized which would require a single clock input rather than the clock and $\overline{\text{clock}}$ inputs required with the present array. Every time a clock and $\overline{\text{clock}}$ input is applied to the array 40, the array sequences from one pixel to the next sequential pixel. Thus, the clock pulses enable the plurality of pixels in the array to be sequentially polled.

The array 40 also includes an end-of-line output 54 which has an output thereon when the last pixel in each of the 38 rows of the array is polled. The present array is a 12×38 array and after every 14 clock pulses, the end of a line will be reached and an output will be outputted on line 54. In fact, each row of the present array includes 12 active pixels and two dummy pixels which must be clocked to provide an output on the end-of-line output 54 so that 14 pulses must be applied before the end of the line is reached. When an output is present on line 54, transistor 56 is rendered conductive and a signal is established on line 58 indicating that the end of a line of the array has been reached. The signal on line 58 is directed through a digital non-inverter 60 to the input of a flip-flop 62. The flip-flop 62 provides end-of-line (EOL) and not end-of-line ($\overline{\text{EOL}}$) signals on lines 64 and 66 which are respectively directed through digital inverters 68 and 70 to inputs of the array 40. The present array requires an EOL and $\overline{\text{EOL}}$ inputs to effect sequencing of the array from one line to the next sequential line.

After the array has polled all of the 12 active pixels and two dummy pixels in each of the 38 lines in the array an end of frame signal (EOF) will be stablished on the output 72 of the array 40. An output on line 72 will effect conduction of transistor 74 to thereby establish a signal on line 76 indicating that the end of a frame has been reached. The signal on line 76 can be directed through a digital non-inverter 77 and utilized to reset the array internally after all of the lines have been polled. It should be apparent that each pixel of the array will be sequentially polled each time an item 12 is to be inspected.

The array 40 is operable to sequentially sense information from each of the pixels which sense the condition of an object 12 which is to be sensed by the array. The array 40 includes an output line 80 on which a serial analog signal is established indicative of the information sensed by each pixel as the array examines an object 12. Each serial analog signal will include a plurality of serial analog bits wherein each bit is indicative of the information sensed by one of the pixels of the array 40. If a plurality of objects are sequentially passed by the array, a plurality of serial analog signals will be generated on line 80.

The analog signal on line 80 is directed to an input of a charge pulse amplifier 82. The charge pulse amplifier 82 measures the charge put on each pixel of the array as the various pixels are sequentially polled. It should be appreciated that the array preferably comprises a plurality of light sensing diodes. When the diodes sense light, they discharge much the same as a capacitor discharges. When the array is polled, a charge will be replaced on the capacitor of the array and the amount of charge replaced on the capacitor will be indicative of the amount of light sensed by the array. The output of the charge pulse amplifier 82 is a serial analog signal, schematically shown at 83, composed of a plurality of pulses representative of the information stored in each of the pixels of the array 40 and is directed to an integrating circuit 84. The integrator 84 integrates the waveform 83 to establish a wave form similar to wave form 86 having a plurality of sharp pulses wherein each pulse is representative of the information sensed by one of the pixels of the array 40. A reset 88 is provided to reset the integrator circuit 84 each time a pulse from the analog signal 83 is applied thereto. A clock signal 90 can be applied to the integrator reset 88 to synchronize the integrator reset with the analog pulses being applied to the integrator circuit 84 by the charge pulse amplifier 82.

The output of the integrator 84 is directed to a sample and hold circuit 92 which also has a clock signal applied on an input line 94 thereto. The clock signal synchronizes the sample and hold circuit 92 with the pulses in the signal 86 applied from the integrator 84. The output of the sample and hold circuit 92 is a boxcar wave similar to that disclosed at 96. The output of the sample and hold circuit 92 is directed along the output line 98 to the input of the threshold circuit 24. The sample and hold circuit 92 establishes the boxcar wave 96 which is a square wave signal having various amplitudes indicative of the level of the output signals from each pixel during each discrete reading of a pixel. The various levels of the boxcar wave 96 are indicative of the readings of the pixel where, for example, the highest level would be indicative of a white area being read by the pixel while the lowest level would be indicative of a black area being read by the pixel. Levels in between the 100% white or the 100% black level would be indicative of various grey levels. Thus, the output of the sample and hold circuit 92 is a delayed square wave having various levels indicative of black, white or various grey levels between black and white.

The boxcar output of the sample and hold circuit 92 is directed along line 98 to the threshold circuit 24. The threshold circuit will automatically set a threshold signal level which may vary from one serial signal from a polling of the array 40 to the next and above which signals in the boxcar wave 96 will be classified white and below which signals will be classified black. This provides dynamic tracking of both sides, i.e., high and low, of the data from the plurality of pixels while allowing the analog information from the array 40 to be converted to binary form.

Figure 3:
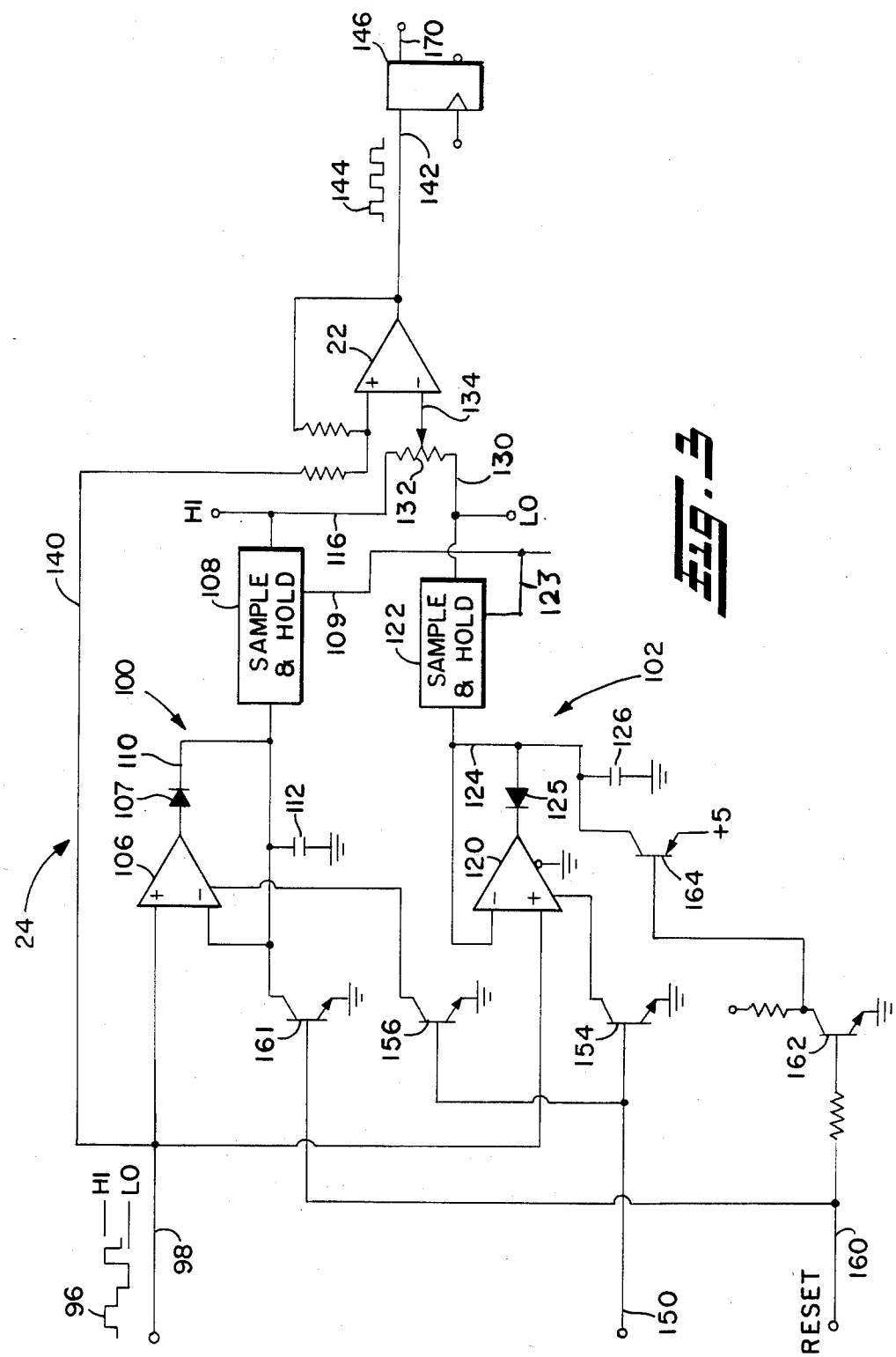
FIG. 3 is a detailed schematic of the threshold and comparator circuits.

The threshold circuit 24, as is more fully illustrated in FIG. 3, includes a high peak detector 100 and a low peak detector 102. The high peak detector 100 is operable to hold a signal therein representative of the highest peak sensed in a boxcar wave 96 for each serial analog signal indicative of the reading of the array 40. The low peak detector 102 is operable to hold a signal therein which is representative of the lowest peak sensed in a boxcar wave 96 for each serial analog signal from the array 40.

The high peak detector 100 includes an operational amplifier 106 and a sample and hold circuit 108. The input on line 98 is from the sample and hold circuit 92 and is directed through the operational amplifier 106 and diode 107 along line 110 to the sample and hold circuit 108. A capacitor 112 is connected to line 110 and charges to a level proportional to the highest signal received on the line 98 during each serial analog signal and diode 107 prevents capacitor 112 from discharging through amplifier 106. Sample and hold circuit 108 holds a charge therein which is proportional to the highest peak sensed by the peak detector 100 in each serial analog signal. A clock input 109 is provided to sample and hold circuit 108 to clock data from each frame into the sample and hold circuit 108. The sample and hold circuit is clocked once during each frame to enter a signal which is proportional to the highest signal received on line 98 during the particular serial analog signal. The output of the sample and hold circuit 108 is directed along line 116 and is a signal proportional to the highest peak sensed in the serial wave form 96 from the sample and hold circuit 92.

The input on line 98 is also directed to an amplifier 120 and a sample and hold circuit 122 which form the low peak detector 102. The output of amplifier 120 is directed through diode 125 along line 124 to the input of the low sample and hold circuit 122 and to a capacitor 126 which discharges to a level proportional to the lowest peak sensed on the input line 98 during each serial analog signal. The diode 125 prevents capacitor 126 from being charged by the output of amplifier 120 but allows capacitor 126 to discharge through amplifier 120. The low sample and hold circuit 122 is charged proportional to the lowest peak sensed on line 98. A clock input 123 is provided to sample and hold circuit 122 to clock data from each frame into the sample and hold circuit 122. The sample and hold circuit 122 is clocked once during each frame to enter a signal which is proportional to the lowest signal received on line 98 during a particular frame. The output of the sample and hold circuit 122 is directed along line 130 and is proportional to the lowest peak sensed in each serial analog signal input on line 98.

The output from the high peak detector 100 is directed along line 116 and the output from the low peak detector 102 is directed along line 130. Lines 116 and 130 are connected to the input of the comparator 22 across a resistance divider 132. The resistance divider 132 could be adjustable and the output on line 134 is a threshold signal or set point dependent upon the highest and lowest peaks sensed in each frame and which determines the crossover point or set threshold above which comparator 22 converts the bits of the serial analog signal to a one and below which comparator 22 converts the bits of the serial analog signal to a zero. Thus, the threshold circuit 24 provides dynamic compensation for tracking the high and low sides of each serial analog signal from the array 40.

The analog input on line 98 is also directed along line 140 to an input of the comparator 22. The comparator 22 is operable to compare the boxcar wave form 96 on line 140 with the threshold as set on line 134. This allows the comparator to establish a digital output on line 142 as is schematically shown at 144. The digital output on line 142 is directed through a synchronizing flip-flop 146 to the input of RAM 28 associated with the central processing unit 30 as is more fully disclosed in FIG. 1.

The automatic threshold circuit 24 allows the extraction of accurate data by the optical inspection system. It extracts data of a scene based on the highest value and the lowest value within the scene. This provides for dynamic compensation and allows compensation for changes in ambient light conditions which can vary the threshold level. For example, if a cloud were to pass by a window which directed light toward the object 12, the system would automatically compensate and track out variations in the light conditions. Basically, the system divides the difference between the high peak value and the low peak value in half or at any other proportional value set by resistance divider 132 and looks at the highest and lowest signals and defines a mid-point or threshold setting in between the highest and lowest signals. The mid-point or set threshold is compared with each bit of the analog information on line 140 and each bit on line 140 which is above the threshold or mid-point is converted to a one binary set which is indicative of a white signal and each bit below the threshold is converted to a zero binary bit which is indicative of a black signal.

It should be appreciated that the peak detectors 100 and 102 sense the peaks associated with each serial analog signal indicative of the reading of the pixels of the array 40. Thus, the threshold may change every time a serial analog signal is received from the array 40 if the highest and lowest peaks sensed in each signal vary from one serial analog signal to the next. After a time a signal is received by the peak detectors 100 and 102, signals are established on lines 116 and 130 which set the threshold which is reset for each new frame. While the peak detectors 100 and 102 operate on a real time basis, it should be appreciated that the outputs of the sample and hold circuits 108 and 122 will be one frame behind the signals sensed from the array on line 140. Each item 12 which is to be sensed is scanned repeatedly as it moves by the array 40. Thus, the threshold which is actually set and utilized is a threshold which was sensed on the previous scan of the item 12 which is to be examined and which will be repeatedly scanned as it passes in front of the array 40. Thus, the threshold set point which is compared to a real time serial analog signal on line 140 indicative of an item 12 currently being inspected will be the threshold set by the previous serial real time analog signal from the previous scan of the item 12.

The threshold circuit 24 also includes an input on line 150 which is a peak strobe input to tell the peak detectors 100 and 102 when to look at each step of the serial analog signal applied thereto. The peak strobe signal on line 150 is directed to and effects non-conduction of transistors 154 and 156 which condition the amplifiers 106 and 120 to conduct the signals from line 98. In addition, a threshold reset signal is provided on line 160. The threshold reset signal is derived from the end of frame information on line 76. The EOF signal indicates the end of the serial analog signal from the array 40 after the array 40 has completed its sequential polling of the pixels and is directed to a transistor 162 to effect conduction thereof and to a transistor 161 to effect conduction thereof. Conduction of transistor 162 causes a transistor 164 to conduct which charges capacitor 126, thereby resetting the low peak detector 102. Conduction of transistor 161 discharges capacitor 112 thereby resetting the high peak detector 100.

The output of the synchronization flip flop 146 is directed along line 170 to the RAM 28 associated with the central processing unit 30. The output from the synchronization flip-flop 146 is a serial binary signal having bits indicative of white or black being sensed by each pixel of the array 40. The central processing unit 30 then compares the binary signal directed to the RAM 28 with a reference signal stored in reference RAM 32 and makes a decision on whether the item 12 sensed is a good or bad item. If a bad item is present, the central processing unit will direct a signal along line 31 to the reject mechanism 34 to reject the bad object 12.

Figure 4:
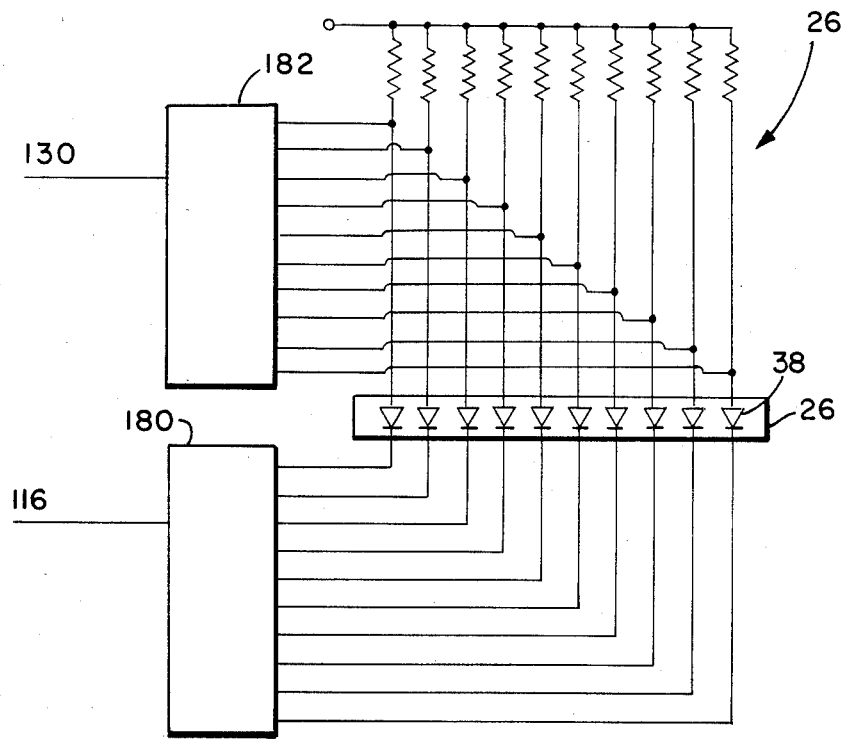
FIG. 4 is a detailed schematic of the indicator means for indicating the contrast between the highest peak and the lowest peak of each analog signal.

The outputs from the sample and hold circuits 108 and 122 are directed to indicator means 26, more fully disclosed in FIG. 4, which is responsive to the high peak signal from the sample and hold circuit 108 on line 116 and the low peak signal from the sample and hold circuit 122 on line 130 for generating a visual indication of the difference or contrast between the high and low signals. The difference between the high and low signals is indicative of the light level and contrast sensed by the array 40. It is desirable to have as high a light level as possible without saturating the array 40 in order to obtain the highest signal to noise ratio to prevent erroneous readings due to noise. To this end, a plurality of indicator lights 38 which are arranged in a bar graph display are lit to visually indicate both the high and low signals to give a visual indication of signal contrast and light level to the user of the system. The output signal of the high sample and hold circuit 108 is directed along line 116 to a ten-level comparator and LED driver 180 and the output from the low sample and hold circuit 122 is directed along line 130 to a ten-level comparator and LED driver 182. The ten-level comparators 180 and 182 have ten preset, different, fixed levels set therein and provide an output on each level when the input signal to the ten-level comparator is equal to or greater than the fixed level associated with the level which is actuated. If the input is less than a particular fixed level, then that particular level will not be actuated. Each of the outputs of the high ten-level comparator 180 turn on one associated LED 38 when the associated fixed level of the LED is equal to or less than the level of the input signal on 116. Each of the outputs of the low ten-level comparator and LED driver 182 turn off one associated LED 38 when the input on line 130 is equal to or greater than the associated fixed level of the ten-level comparator 182. Thus, the number of LED's 38 actuated is indicative of the difference between the high and low peak signals and gives an indication of contrast and light level on the object 12 being sensed. This allows the operator to adjust the contrast by adjusting the light source and position of the array 40 to control the contrast that the system sees. This is comparable to adjusting the contrast and brightness on a TV set. The bar graph display indicator 26 gives the operator of the system instant information relative to the strengths of various signals and tells the operator if the device is saturated (i.e., all of the lights would be lit), how much contrast is present (i.e., the number of lights lit), or if there is not enough light (i.e., no lights lit). The operator can then adjust the intensity of the lights 14, direction, item orientation and location and array location and orientation to ensure maximum contrast and light level. For example, if the input signal 116 had a level higher than the first eight levels of the high comparator 180, but lower than the last two levels, then the first eight LED's 38, counting from the right in FIG. 4, would be turned on. If the input 130 to the low level comparator 182 was higher than the first three levels set in the low level comparator 182 and lower than the rest of the levels, then the first three LED's 38, counting from the right in FIG. 4, would be turned off. The net result would be that five LED's, i.e., the eight turned on by the high level comparator 182, minus the three turned off by the low level comparator 182 would be lit. The five LED's lit would be the 4th, 5th, 6th, 7th and 8th, counting from the right in FIG. 4.

Thus, the number of LED's 38 lit for a particular signal give a visual indication of contrast and the location of the lit LED's 38 on the bar graph display 26 give an indication of the relative strengths of the high and low peak signals and thus the light level. The high peak signal turns on the LED's and the low peak signal turns off the LED's 38 and the net number of LED's lit is indicative of the difference between the high and the low signals. It should be appreciated that by using the bar graph display 26, an active readout of contrast can be provided and the operator can adjust the instrumentation until a certain degree of contrast is indicated by the bar graph display 26. This is the same as adjusting the brightness and contrast of a TV except that no TV screen is provided and the LEDs satisfy the viewing requirements. The combination of the bar graph display 26 and the dynamic threshold circuit 24 allows the user to operate the system over a wide range of conditions. It will be desirable (but not absolutely necessary) to have at least a 25% contrast in the information sensed by the array 40. If at least a 25% contrast is not obtainable, the information sensed by the array will not be reliable. Thus, if ten diodes are provided in the bar graph display 26, it will be the operator's duty to ensure that at least three of the diodes are lit, indicating 30%, i.e., at least 25% contrast.

Additionally, it is desirable that the 10th LED (i.e., the 10th one from the right in FIG. 4) blink while it is lit to indicate that the unit has reached saturation. This will allow the operator to adjust the system 10 to decrease the high peak signal when saturation occurs. During normal operation of the system, it is desirable to have the bar graph display 126 light as near the top level as possible without lighting the 10th LED from the right which will indicate saturation. This increases the signal to noise level and prevents erroneous signals due to noise. Normally the operator will adjust the system so that the higher LED's, i.e. 8th, 9th and 10th from the right are lit and then will adjust the system so that the 10th LED from the right goes off for maximum performance.

While the present optical inspection system 10 has been described as viewing an object 12, it should be appreciated that various information could be sensed from various objects. For example, while the particular optical inspection system 10 has been designed to identify labels or graphics on bottles or other packages, it could be utilized to inspect other items, inspect configuration of parts, or provide other inspection tasks. For the purposes of this invention, the term labels has been loosely used to include labels or other graphics or item configurations which can be inspected to determine information from an inspected item. It is contemplated that the array 40 will be fixed and that the objects 12 will sequentially move past the array 40. Every time the array 40 reads the information on one of the objects 12 passing thereby a serial analog signal will be established from the array 40 indicative of the information sensed by each of the pixels. Thus, when a plurality of items pass in front of the array, a plurality of serial analog signals will be sequentially generated as each item 12 passes the array 40.

While the present invention has been disclosed as sensing reflected light from an inspected item, it should be appreciated that other types of radiation other than light could be utilized without departing from the scope of the present invention. Additionally, radition could be sensed to determined information from an inspected item which is reflected radiation or absorbed radiation. For example, the item to be inspected could be back lit and the not absorbed radiation inspected.

From the foregoing, it should be apparent that a new and improved optical inspection system has been provided which includes a light source 14 for illuminating an item 12 to be inspected, an optical reader or array 16 responsive to the light reflected from the item 12 to be inspected for deriving a serial analog signal indicative of the information sensed. A threshold circuit 24 is provided for setting a dynamic threshold used to convert the analog signal into a binary signal indicative of the information sensed in the item to be inspected. The threshold circuit 24 includes a high peak detector 100 and a low peak detector 102 responsive to the highest and lowest peaks, respectively, in the analog signal from the array 40. A threshold setting means 132 is responsive to the high peak signal and the low peak signal for setting a dynamic threshold therebetween. A comparator means 22 compares the analog signal with the set threshold to convert the analog signal to a binary signal indicative of the information sensed on the inspected item 12. The binary signal has a high condition when the analog signal exceeds the set threshold and a low condition when the analog signal is less than the set threshold. An indicator means, preferably in the form of a bar graph display 26, is responsive to the high peak and low peak signals for generating a visual indication of the difference between the high peak and low peak signals on the light emitting diodes 38.

What I claim is:

1. An optical system for deriving information from an inspected item comprising a radiation source for illuminating the inspected item, a reader responsive to the radiation from said radiation source which is indicative of information sensed on the inspected item for sequentially establishing a plurality of analog signals indicative of the information sensed on the inspected item, each of said signals beings responsive to changing ambient radiation, a threshold circuit for setting a dynamic threshold used to convert each of said analog signals into a binary signal indicative of the information sensed on the inspected item and for compensating for changing ambient radiation, said threshold circuit being responsive to the highest peak in one of said analog signals and generating a high signal indicative thereof and being responsive to the lowest peak in said one analog signal and generating a low signal indicative thereof, said threshold circuit including threshold setting means responsive to said high signal and said low signal for setting a threshold between said highest peak and said lowest peak which dynamically compensates for changing ambient radiation, comparator means for comparing each of said analog signals with said set threshold and converting each of said analog signals to a binary signal indicative of the information sensed on the inspected item which has a high condition when the analog signal exceeds said set threshold and a low condition when said analog signal is less than said set threshold, and indicator means responsive to said high signal and said low signal for generating a visual indication of the difference between said high and low signals and the magnitude of said high and low signals.

2. An optical system as defined in claim 1 wherein said indicator means includes a plurality of indicating elements, said high signal effecting energization of a predetermined number of said indicating elements which is dependent upon the magnitude of said high signal, said low signal effecting deenergization of a predetermined number of said energized indicating elements which is dependent upon the magnitude of said low signal, and wherein the number of indicating elements ultimately energized is indicative of the magnitude and difference in magnitude between said high signal and said low signal to thereby provide a visual indication of the contrast and brightness on the inspected item.

3. An optical system as defined in claim 2 wherein said indicating elements comprise light emitting diodes and further including a high peak detector responsive to the highest peak in said one analog signal for generating said high signal indicative thereof and a low peak detector responsive to the lowest peak in said one analog signal for generating said low signal indicative thereof.

4. An optical system as defined in claim 3 wherein said plurality of light emitting diodes form a bar graph display and are arranged in a row, said high signal effects energization starting at one end of said row of a sequential number of said light emitting diodes which number is dependent upon the magnitude of said high signal and said low signal effects deenergization starting at said one end of said row of a sequential number of said light emitting diodes which number is dependent upon the magnitude of said low signal and wherein the number of said light emitting diodes which remain sequentially energized is indicative of the magnitude and the difference of magnitude between said high signal and said low signal.

5. An optical system as defined in claim 2 wherein said indicating means further includes first and second multilevel comparators associated with said high and low signals, respectively, each of said multilevel comparators including a plurality of fixed levels therein, each of said fixed levels being associated with one of said indicating elements, said first multilevel comparator comparing the magnitude of said high signal with the plurality of fixed levels therein and effecting energization of each indicating element associated with a fixed level which is exceeded by said high signal, said second multilevel comparator comparing the magnitude of said low signal with the plurality of fixed levels therein and effecting deenergization of each indicator element associated with a fixed level which is exceeded by said low signal to enable the plurality of indicating elements which are energized to be indicative of the magnitude and the difference between said high and said low signals.

6. An optical system as defined in claim 1 further including storage means having a reference stored therein which is indicative of the information which should be sensed from the inspected item if the inspected item is a good item and second comparator means for comparing said reference with the information contained in the binary signal which is indicative of the information sensed on the inspected item to determine if the inspected item is a good or bad item.

7. An optical system as defined in claim 6 further including reject circuitry for establishing a reject signal in the event that said second comparator means determines that the inspected item is a bad item.

8. An optical system as defined in claim 4 further including storage means having a reference stored therein which is indicative of the information which should be sensed from the inspected item if the inspected item is a good item, and second comparator means for comparing said reference with the information contained in the binary signal which is indicative of the information sensed on the inspected item to determine if the inspected item is a good or bad item.

9. An optical system as defined in claim 8 further including reject circuitry for establishing a reject signal in the event that said second comparator means determines that the inspected item is a bad item.

10. An optical inspection system as defined in claim 5 wherein the indicating element which is associated with the highest fixed level of said first multilevel comparator is operable to provide a distinctive signal when energized which is indicative of the system being saturated.

11. An optical system for sequentially inspecting a plurality of items, comprising a radiation source for directing radiation to the items to be inspected, a reader responsive to radiation from said radiation source which is indicative of information sensed on the inspected item for sequentially establishing a plurality of analog signals each of which has a plurality of serial bits indicative of the information sensed on the inspected item, said reader also being responsive to changing ambient radiation and including a plurality of sensor elements arranged in an array and which are sequentially polled each time the item is to be inspected to establish one of said analog signals wherein each serial bit of analog information for each inspected item is indicative of the information sensed on the inspected item by one of said sensor elements, a threshold circuit for setting a dynamic threshold used to convert each of said analog signals into a binary signal having a plurality of serial binary bits indicative of the information sensed on the inspected item by each sensor element and for compensating for changing ambient radiation, said threshold circuit being responsive to the highest peak in one of said analog signals from said plurality of sensor elements and generating a high signal indicative thereof and being responsive to the lowest peak in said one analog signal from said plurality of sensor elements and generating a low signal indicative thereof, said threshold circuit including threshold setting means responsive to said highest signal and said lowest signal for setting a threshold between said highest and said lowest peak, and comparator means for comparing each bit of each of said analog signal from each of said plurality of sensor elements with said set threshold and converting each bit of each of said analog signals to a bit of a binary signal to establish a binary signal having a plurality of serial bits indicative of the information sensed on the inspected item by each of said plurality of sensor elements, each bit of said binary signal having a high condition when the analog signal from each sensor element exceeds said set threshold and a low condition when said analog signal from each sensor element is less than said set threshold and indicator means responsive to said high signal and said low signal for generating an indication of the magnitude of said high and low signals and difference between said high and low signals from said plurality of sensor elements.

12. An optical system as defined in claim 11 further including storage means having a reference stored therein which is indicative of the information which should be sensed by said plurality of sensor elements from an inspected item if the inspected item is a good item and second comparator means for comparing said reference with the information contained in the binary signal from said plurality of sensor elements which is indicative of the information sensed on the inspected item to determine if the inspected item is a good item or a bad item.

13. An optical system as defined in claim 12 further including reject circuitry for establishing a reject signal in the event that said second comparator means determines that the inspected item is a bad item.

14. An optical system as defined in claim 12 wherein said indicator means includes a plurality of indicator elements, said high signal effecting energization of a predetermined number of said indicating elements which is dependent upon the magnitude of said high signal, said low signal effective deenergization of a predetermined number of said energized indicating elements which is dependent upon the magnitude of said low signal, and wherein the number of indicating elements ultimately energized is indicative of the difference in magnitude between said high signal and said low signal from said plurality of sensor elements to thereby provide a visual indication of the radiation contrast and magnitude on the inspected item.

15. An optical system as defined in claim 14 wherein said indicator elements comprise light emitting diodes and said plurality of indicating elements are arranged in a row and form a bar graph display.

16. An optical system as defined in claim 15 wherein said high signal effects energization, starting at one end of said row, of a sequential number of said light emitting diodes which number is dependent upon the magnitude of said high signal and said low signal effects deenergization starting at said one end of said row of a sequential number of said light emitting diodes which number is dependent upon the magnitude of said low signal and wherein the number of said light emitting diodes which remain sequentially energized is indicative of the magnitude and the difference between said high signal and said low signal.

17. An optical system as defined in claim 16 wherein said indicating means further includes first and second multilevel comparators associated with said high and low signals, respectively, each of said multilevel comparators including a plurality of fixed levels therein, each of said fixed levels being associated with one of said light emitting diodes, said first comparator comparing the magnitude of said high signal with the plurality of fixed levels therein and affecting energization of each light emitting diode associated with a fixed level which is exceeded by said high signal, said second comparator comparing the magnitude of said low signal with the plurality of fixed levels therein and effecting deenergization of each light emitting diode associated with a fixed level which is exceeded by said low signal to enable a plurality of light emitting diodes to be energized and wherein the number of energized light emitting diodes is indicative of the magnitude and the difference between said high and low signals.

18. A label inspection system for sequentially inspecting a plurality of items having labels thereon, comprising a light source for illuminating the items to be inspected, an optical reader responsive to the light reflected from the inspected item from said light source and to changing ambient radiation for sequentially establishing a plurality of analog signals each of which have a plurality of serial bits indicative of the information sensed on the inspected item, said optical reader including a plurality of sensor elements arranged in an array and which are sequentially polled each time an item is to be inspected to establish one of said analog signals which has a plurality of serial analog bits wherein each bit is indicative of the information sensed by one of said polled sensor elements, a threshold circuit for setting a dynamic threshold used to convert each of said serial analog signals into a serial binary signal wherein each bit of information is indicative of the information sensed by one of said polled sensor elements for each inspected item and for compensating for changing ambient radiation, said threshold circuit including a high peak detector responsive to the highest peak in one of said serial analog signals and generating a high signal indicative thereof, a low peak detector responsive to the lowest peak in said one serial analog signal and generating a low signal indicative thereof, and threshold setting means responsive to said high signal and said low signal for setting a threshold between said highest peak and said lowest peak, comparator means for comparing each of said serial analog signals with said set threshold and converting each of said serial analog signals to a serial binary signal indicative of the information sensed on the inspected items, each bit of said serial binary signal having a high condition when the analog signal exceeds said set threshold and a low condition when said analog signal is less than said set threshold, and indicator means responsive to said high signal and said low signal for generating a dynamic visual indication of the difference between said high and low signals.

19. A label inspection system as defined in claim 18 wherein said indicator means includes a plurality of indicating elements, said high signal effecting energization of a predetermined number of said indicating elements which is dependent upon the magnitude of said high signal, said low signal effecting deenergization of a predetermined number of said energized indicating elements which is dependent upon the magnitude of said low signal, and wherein the number of indicating elements ultimately energized is indicative of the magnitude and the difference in magnitude between said high signal and said low signal to thereby provide a visual indication of the brightness and contrast on the inspected item.

20. A label inspection system as defined in claim 19 wherein said indicating elements comprise light emitting diodes.

21. A label inspection system as defined in claim 20 wherein said plurality of light emitting diodes are arranged in a row, said high signal effects energization starting at one end of said row of a sequential number of said light emitting diodes which number is dependent upon the magnitude of said high signal and said low signal effects deenergization starting at said one end of said row of a sequential number of said light emitting diodes which number is dependent upon the magnitude of said low signal and wherein the number of said light emitting diodes which remain sequentially energized is indicative of the magnitude and the difference in magnitude between said high signal and said low signal.

22. A label inspection system as defined in claim 21 wherein said indicating means includes first and second multilevel comparators associated with said high and low signals, respectively, each of said multilevel comparators including a plurality of fixed levels therein, each of said fixed levels being associated with one of said light emitting diodes, said first multilevel comparator comparing the magnitude of said high signal with the plurality of fixed levels therein and effecting energization of each light emitting diode associated with a fixed level which is exceeded by said high signal, said second multilevel comparator comparing the magnitude of said low signal with the plurality of fixed levels therein and effecting deenergization of each light emitting diode associated with a fixed level which is exceeded by said low signal to enable the plurality of light emitting diodes which are energized to be indicative of the magnitude and the difference between said high and said low signals.

23. An optical system as defined in claim 22 further including storage means having a reference stored therein which is indicative of the information which should be sensed from the inspected item if the inspected item is a good item and second comparator means for comparing said reference with the information contained in the serial binary signal which is indicative of the information sensed on the inspected item to determine if the inspected item is a good or bad item.

24. An optical system as defined in claim 23 further including reject circuitry for establishing a reject signal in the event that said second comparator means determines that the inspected item is a bad item.

* * * * *